United States Patent [19]

Marcote et al.

[11] 3,976,450
[45] Aug. 24, 1976

[54] GAS SAMPLE PREPARATION SYSTEM AND METHOD

[76] Inventors: Roland Marcote, 19519 Sherman Way, No. 7, Reseda, Calif. 91335; Steve Eisenberg, 5658 Fearing St., Santa Susana, Calif. 93063; Ramesh Chand, 2600 Wilshire Blvd., Suite 309, Los Angeles, Calif. 90057; Herman Haase, 19047 E. Lynfield, Glendora, Calif. 91740

[22] Filed: July 23, 1974

(Under Rule 47)

[21] Appl. No.: 491,026

Related U.S. Application Data

[63] Continuation of Ser. No. 320,144, Jan. 2, 1973, abandoned.

[52] U.S. Cl. ................................ 55/158; 55/269; 55/270; 73/23; 73/421.5 R
[51] Int. Cl.² ........................................ B01D 53/22
[58] Field of Search ............... 55/16, 158, 73, 269, 55/270; 73/61.1 R, 421.5 R, 23, 28

[56] References Cited
UNITED STATES PATENTS

| | | | |
|---|---|---|---|
| 3,545,931 | 12/1970 | McKinley, Jr. | 55/16 |
| 3,550,355 | 12/1970 | Remus et al. | 55/16 |
| 3,674,435 | 7/1972 | Van Luik, Jr. | 55/16 |
| 3,721,065 | 3/1973 | Robicheaux et al. | 55/16 |

OTHER PUBLICATIONS

Dynascience Publication 42M671, effective date prior to 1/2/72.
Advances in Air Pollution Control Technology, 7a American Institute of Chemical Engineers, 5–69.
Ind. Lab. (U.S.A.), vol. 37, No. 6, June, 1971, pp. 949 and 950.

*Primary Examiner*—John Adee
*Attorney, Agent, or Firm*—Poms, Smith, Lande & Glenny

[57] ABSTRACT

A gas sample flowing through the lower chamber of a diffusion cell diffuses through a membrane into the upper chamber at a rate above a determined minimum. As the sample diffuses through the membrane, substantially all of the water and any particulates are removed from the gas. A clean carrier gas flows through the upper chamber at a constant rate to dilute the diffused gas and convey it to gas analyzers. Upon acquisition, a gas sample is maintained at a temperature above its dew point until it passes from the lower chamber and the membrane is maintained at a substantially constant temperature.

10 Claims, 6 Drawing Figures

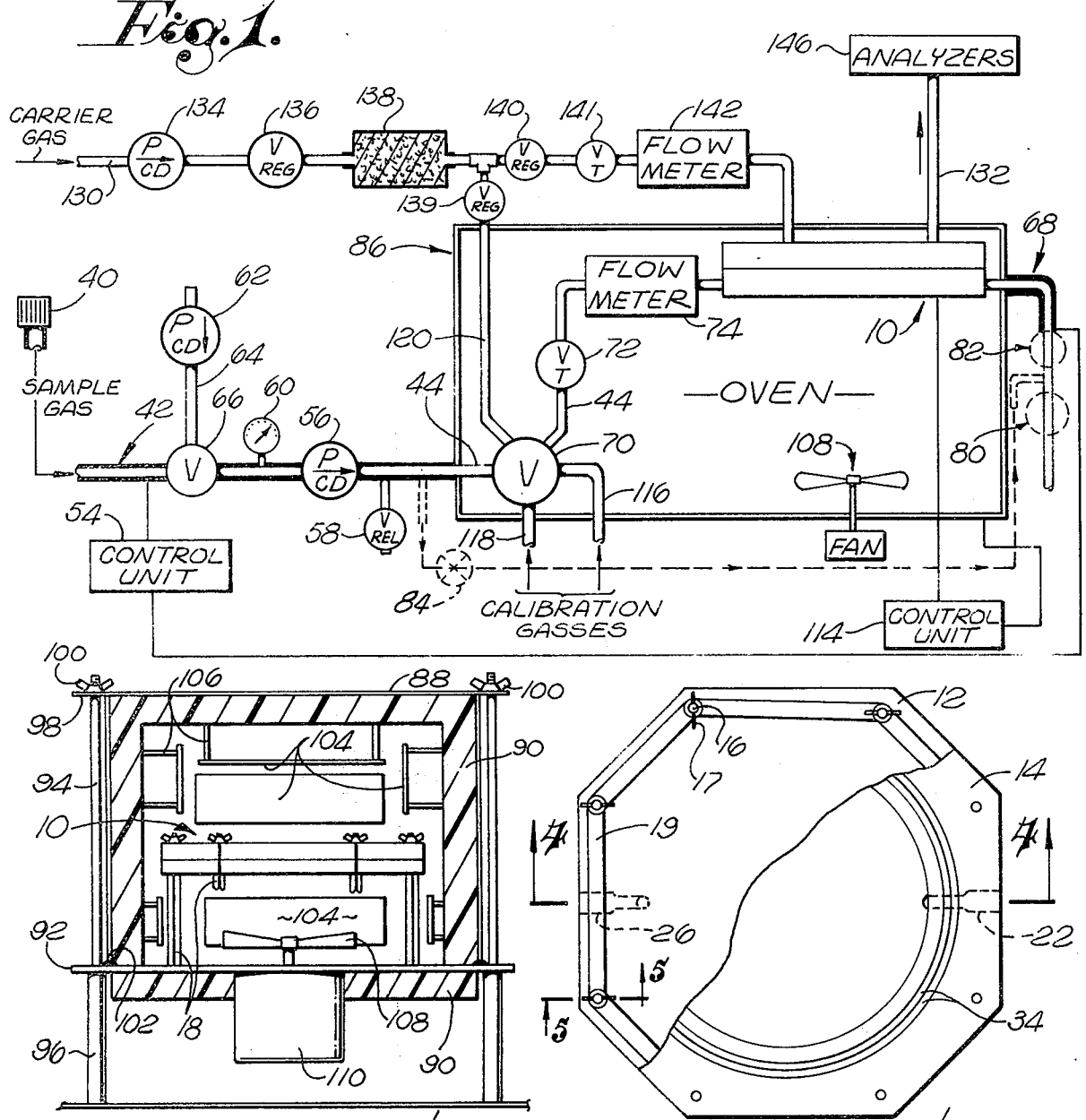
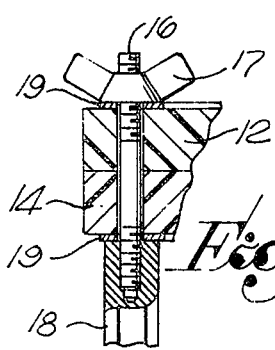
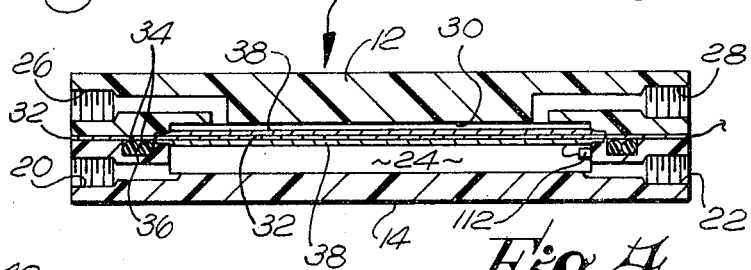
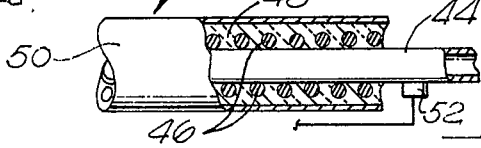

GAS SAMPLE PREPARATION SYSTEM AND METHOD

CROSS REFERENCE TO RELATED APPLICATION

This application is a continuation of U.S. patent application Ser. No. 320,144, filed Jan. 2, 1973, now abandoned.

BACKGROUND OF THE INVENTION

Oxides of nitrogen, sulfur dioxide, carbon monoxide, partly oxigenated hydrocarbons and other gases have become serious atmospheric pollutants. Significant atmospheric concentrations of such gases in large metropolitan and industrial areas from automobiles, industrial stack wastes, and consumption of certain fuels in homes and power generating facilities can cause serious pollution problems. Conditions such as smog are recognized as very detrimental to human and animal health, with the resulting eye and lung irritation being the most vexatious result. Such atmospheric contamination can also inhibit and destroy plant growth as well.

Sulfur dioxide, which has been found to be second only to carbon monoxide as a major pollutant source, is known to be extremely dangerous in view of its corrosive and potentially poisonous characteristics. It causes irritation and inflammation of the eyes and respiratory tract, and in moist air and fogs, combines with water to form sulfurous acid which is slowly oxidized into sulfuric acid.

The ability to continuously monitor the concentration of oxides of nitrogen, sulfur dioxide, carbon monoxide and other atmospheric pollutants has become increasingly important in remedying and controlling such conditions. Presently a number of pollutant concentration gas analyzers are available including those incorporating coulometric, colorimetric, electrical and thermal conductivity as well as infrared and ultraviolet method of analysis. More recently, electrochemical apparatus, such as those described in U.S. Pat. Nos. 3,622,487 and 3,622,488, have become available.

For the most part, these gas analyzers operate with a continuous supply of a representative gas sample taken from the environment under analysis. However, particulate matter, water and certain gases can interfere with the operation of the analyzer and must be removed, and the pressure and temperature of the sample must be regulated in many instances to avoid irregularities in the operation of or damage to the analyzer. In this regard, industrial stack gases, automobile exhausts and similar combustion gases present the most serious problems. Such combustion gases frequently contain soot, fly ash and water vapor which, if not removed from the sample, would quickly render most gas analyzer instruments inoperative. Moreover, the high temperatures and pressure fluctuations produced across any given cross-section of a stack, as well as the periodic variations at any point, can result in substantial inaccuracies for certain analyzers. In addition, if a gas sample containing water vapor is allowed to cool below its dew point, the condensed water vapor can remove significant amounts of such water soluble gases as $SO_2$, $NO_2$ and others, from the sample stream, thus reducing the concentration of those gases available to the analyzer.

Previous analyzers intended to operate within industrial stacks aare subject to interference or inaccuracy from one or more of these causes in spite of special sample conditioning systems. Attempts were made to supply "clean" gas samples to remote analyzers through banks of filters, chemical scrubbers and condensate removal apparatus that would eliminate particulate matter, water and interfering gases from the sample while cooling it to desired temperatures. However, such complex conditioning systems proved unduly cumbersome, fragile, and expensive and were not generally suitable for unattended operation in conjunction with a continuously operating analytical system. In addition, losses of certain water soluble gases are inherent in such system so that the concentrations in the samples reaching the analyzer could not reliably be correlated with those present in the stack or exhaust stream being monitored.

More recently, proposals have been made for use of a thin-wall transfer tube made of a heat resistant material permeable to the stack gases. With the tube extending across the stack transverse to the gas flow, clean dry air or other carrier gas is passed through the tube from one end to the other at a constant flow rate to carry the gas sample diffusing through the tube walls to an analyzer. In theory, diffusion through the transfer tube is supposed to eliminate the particulate matter and most of the water vapor from the diluted sample of the stack gas delivered to the analyzer. In practice, however, the permeation rate of the transfer tube varies with stack temperature so that a pyrometer control or the like must be used to compensate the analyzer operation for changes in stack temperature. Also, compensations must be made for variations in the stack gas flow rates and pressure, at least below certain minimum levels. Moreover, the capillary openings or other diffusion mechanisms in the transfer tube walls can become rather quickly clogged with soot and the like to reduce the rate at which the gas can enter the sample stream, and the periodic replacements of clogged tubes can be a cumbersome and time-consuming task. High stack temperatures can also distort the wall thickness of the transfer tubes, and thus its permeability, unless certain materials which can withstand the highest anticipated stack temperatures without collapse or distortion are employed.

This invention provides a simple and inexpensive apparatus and method, capable of use with a variety of gas analyzers, for acquiring and preparing representative gas samples without loss of desired components of the gas sample while at the same time eliminating various interfering substances and other sources of analyzer inaccuracies.

SUMMARY OF THE INVENTION

A gas sample flow enters a first chamber of a diffusion cell to pass across a membrane that is readily permeable to the diffusion of certain gases and relatively impermeable to water. That portion of the sample gas which diffuses through the membrane emerges into a second chamber substantially without any of the water previously carried by the diffused gas sample.

In the preferred embodiment of the invention, the gas sample is acquired from the stack or other environment using a probe that acts as a particulate filter. The filtered gas sample is then pumped through the first lower chamber at a constant rate above a given minimum. A portion of the gas sample within the first chamber diffuses through the membrane into a second upper chamber through which a clean carrier gas, consisting of ambient air or an inert gas, flows at a constant rate to dilute the diffused portion of the sample and transport it from the upper chamber to the gas analyzers. The membrane prevents any remaining particulate matter, as well as most of the water in the sample, from reaching the analyzers.

The sample gas is maintained at selected temperatures above its dew point in flowing from the probe through the cell in order to prevent water vapor condensation that would reduce the concentration of certain gases in the sample. The diffusion cell itself is contained in an oven or heater space to maintain the sample gas and membrane within it at a desired constant temperature level. Heating elements and insulation wrapped around conduits used in conveying the sample from the probe to the cell keep the gas sample above its dew point between the probe and the oven.

BRIEF DESCRIPTION OF THE DRAWINGS

FIG. 1 is a schematic representation of a gas sample preparation system in accordance with the invention;

FIG. 2 is an elevational side view of the diffusion cell and oven of one embodiment of the invention;

FIG. 3 is a plan view of the diffusion cell of FIG. 2 with the upper section and membrane partly broken away;

FIG. 4 is a cross-sectional elevational view of the diffusion cell of FIG. 3 taken along the line 4—4 of FIG. 3;

FIG. 5 is a cross-sectional elevational view taken along the line 5—5 of FIG. 3; and, FIG. 6 is a partly cross-sectional view of the temperature controlled conduit employed in one embodiment of the invention.

DESCRIPTION OF THE INVENTION

The particular embodiment of the invention illustrated and described herein is a system for acquiring preparing clean gas samples from stationary, highly polluted sources, such as industrial stack wastes, for application to analyzers designed to monitor $SO_2$ concentrations. As should be apparent, the principles of the invention are applicable to diverse applications for monitoring pollutants from vehicle exhaust systems, ambient atmospheric conditions in cities or industrial areas, and other sources, and may also be employed as a calibration system for gas analyzers.

The complete system shown in FIG. 1 can be considered functionally in four sections: the gas sample acquisition system, the heating system, the diffusion cell and the carrier gas dilution system. The diffusion cell is described first herein to assist in understanding structure and interrelated functions of the acquisition, heating and dilution systems.

THE DIFFUSION CELL

Referring now to FIGS. 2, 3, 4 and 5, a diffusion cell 10 has upper and lower body sections 12 and 14 secured together with their hollow interior cavities concentrically aligned opposite each other to form upper and lower chambers 24 and 30 in a cylindrical cavity. Threaded studs 16 extending through the cell sections 12 and 14 screw into threaded openings at the top of fixed support legs 18 and wing nuts 17 are tightened on the studs' threaded upper ends to clamp the cell sections firmly together on the support legs 18. The support legs 18, preferably formed of steel or other rigid materials, are formed integrally with or otherwise secured at their lower ends to a support plate 92 such as by screws or the like. A thin continuous pressure ring 19 is interposed between the wing nuts 17 and the upper cell section 12 and between the lower cell section 14 and the support legs 18 to distribute the clamping pressure of wing nuts 17 around the perimeter of the cell sections thus avoiding deformation of the cell sections and consequent gas leakage from the chambers 24 and 30. These rings are composed of stainless steel or the like approximately ⅛ inch thick which have been drilled to allow the passage of threaded studs 16 therethrough. Opposed inlet and outlet ports 20 and 22 extend through the sides of lower section 14 to communicate with the lower chamber 24, whereas similarly opposed inlet and outlet ports 26 and 28 communicate through the sides of upper section 12 to communicate with upper chamber 30. A thin circular membrane 32 is clamped at its periphery between the upper and lower sections against two O-rings 34 seated in circular groove 36 to provide a gastight seal around the periphery of the membrane 32, thus separating the upper and lower chambers 24 and 30. The membrane 32 should be smooth and taut when installed. Two thicker, non-resilient circular support pads 38 are also clamped between housing sections 12 and 14 to prevent bulging of the thin resilient membrane 32 into either chamber when the pressure differential between the two chambers becomes large.

In this arrangement, the sample gas being monitored enters the lower chamber 24 through inlet port 20 and passes over membrane 32 before being vented through outlet port 22. In this manner, any particulate matter and the like in the gas sample comes in contact with the lower surface of the membrane where it can fall into the lower chamber, thus inhibiting any substantial build-up on the membrane surface which might clog the membrane or change its permeability. In order to minimize the retention time, that is, the time it takes for any given unit volume of the sample gas introduced at inlet port 20 to reach the far side of membrane 32, the volume of the chamber 24 should be kept relatively small taking into account the expected sample gas concentration.

The desired retention time of the entire system, from probe to analyzer, determines various of the other parameters of the system, such as chamber volumes and carrier gas flow rate. For example, a lower chamber with a diameter of 5.5 inches and a volume of about 38.8 cubic centimeters performs satisfactorily providing a retention time of about 1 second for a sample gas flow rate of about 5 cubic feet per hour. The membrane diameter depends upon the area required for achieving a desired permeation rate. Outlet ports 22 and 28 should both be large enough in relation to the expected sample gas flow rates to avoid any pressure gradients in the chambers which might distort and damage the membrane or result in undesirable retention times.

To avoid condensation, the entire cell 10 is heated, as will be described hereinafter, to a temperature above the dew point of the sample gas entering the cell. The cell components should be able to withstand this temperature without distortion and should be composed of materials that do not react with the gases in the sample, absorb the expected gases, corrode, or otherwise cause any change in the gas sample or the parameters of the cell. Stainless steel and a variety of plastics have been found to be suitable in most situations.

The membrane 32 consists of a thin homogenous sheet of a material that prevents passage of particulate matter and is relatively impermeable to water while readily permitting diffusion of the gases whose concentration is to be measured or analyzed. In addition, the selected membrane material must be capable of withstanding the anticipated operating temperatures. It is also frequently desirable to choose a membrane material which is relatively impermeable to gases that could interfere with the analysis of the particular gases to be analyzed. The thickness of the membrane is determined by the desired permeation rate of the selected membrane material to the particular gases to be analyzed at the expected temperatures. The permeation rate usually decreases as the membrane thickness is increased.

For example, upon determining that the maximum expected dew point of the actual gas sample to be encountered is approximately 150°F, the cell temperature would be maintained at about 170°. In analyzing the concentration of $SO_2$ of about 100 ppm in the gas sample, a dimethyl silicon membrane approximately 1 mil thick is preferred. Dimethyl silicon does not distort at these temperatures and excludes about 99% of the water vapor from the gases diffusing through it. Moreover, it does not react with any gases commonly encountered in such samples and has a relatively low permeability to $H_2S$ and other gases that serves to selectively exclude most of these interfering gases, while being highly permeable to $SO_2$.

Under these conditions, sensitivity ratios of about 5 to 1 are achieved for $SO_2$. This means that for an expected $SO_2$ concentration in the gas sample of about 100 ppm, about 20 ppm would present in chamber 30 where the carrier gas flow rate was about 1 cubic foot per hour. "Sensitivity ratio" is related to permeability and as used herein means the ratio of the concentration of a specific gas ($SO_2$) applied directly to the analyzer compared to the concentration of that same gas in the sample reaching the analyzer through the system after diffusion through the membrane at a specified temperature and carrier gas flow rate. The sensitivity ratio and the carrier gas flow rate are employed to calculate the dilution of the diffused gas sample, as will be explained hereinafter. Other membrane materials, such as Teflon, polyethylene, polyvinylchloride, pellicon, cellophane, RTV (a General Electric Co. silicon-like polymer), MEM (a General Electric Co. silicon containing about 40% polycarbonate), and Zitex (a Chemplast Co. version of Teflon), may be employed depending on the gases and temperatures involved. RTV is normally employed as a sealer but can be cast or spread over a thin perforated sheet of Mylar to form a thin membrane for use in this system. Liquid polymers might also be used.

In some instances, a diffusion cell with more than one membrane defining more than two chambers might be desirable. For example, two membranes could be used to divide an interior cylindrical cavity of the cell into lower, middle and upper chambers with the upper and lower chambers each having their own inlet and outlet ports. By using two membranes with differing selective coefficients of partition, the cell could be made more selective to a particular gas, such as $SO_2$, with each membrane eliminating certain interfering gases. As used herein, a coefficient of partition is defined as the ratio of the permeability of a certain membrane to one gas compared to the permeability of that same membrane to a second gas under the same conditions.

The support pads 36 are composed of relatively thick, porous discs of a material that will not stretch under expected pressure differentials or react with the constituents of the diffused gas sample. The support pads employed are preferably composed of porous air-blown Teflon polymer approximately 30 mils thick, but may be a woven or matted, fibrous material, which does not interfere with the diffusion of gases through the membrane 32.

THE ACQUISITION SYSTEM

Acquisition of a reliable stack gas sample is often difficult because of the temperature and pressure gradients that usually exist across a given cross-section of the stack, and the substantial fluctuations which can be encountered at any given point. Whatever acquisition method is employed in stacks, the problem of fouling due to soot, fly ash and the like must be considered.

The problem of obtaining a representative gas sample can be ideally solved by using a plurality of probes spaced apart at various points across a given laminar flow cross-section of the stack. However, because of the high cost of the probes themselves, these problems may be partially solved by a single probe positioned where an average concentration, pressure and temperature are most likely to occur, or by compensating or correcting the analyzer output.

Temperature changes in the gas sample applied to the membrane, as well as fouling of the membrane, will change the permeation rate of the membrane.

Referring now to FIGS. 1 and 6, a conventional cylindrical sintered stainless steel probe 40 is preferably employed to filter soot, fly ash and the like from the gas sample. The porous cylindrical side walls of sintered steel readily admit the surrounding gas while excluding all but the finest particles of solid materials. One probe employed filters out particles 0.8 microns and larger. To prevent fouling, the probe 40 may be periodically back-flushed or purged by forcing high pressure inert gas or air in the reverse direction out through the probe as required to maintain a sufficient flow of sample gas. A heated conduit 42 conveys the gas sample from the probe 40 to the oven 86 where cell inlet tube 44 connects the conduit 42 to the diffusion cell inlet port 20. A vent tube 68 connected to the outlet port 22 conveys the sample gas from the chamber 24 to the atmosphere. A pump 56 provides a constant flow of sample gas through the conduit 42 to the lower chamber 24, and a relief valve 58 regulates the pressure level in the chamber 24. A vacuum gauge 60 indicates pressure drops in the conduit 42 evidencing, for example, that the probe 40 needs cleaning. A pump 62 supplies reverse high pressure air flow to probe 40 through a line 64 by setting a two position valve 66 to connect the inlet portion and disconnect the remaining downstream end of the conduit 42.

A four position valve 70 provides alternate connection of the cell inlet tube 44 to either two calibration gas lines 116 and 118 or to carrier gas line 120. This permits calibration of the analyzer using the same flow path as the sample gas and cleaning of the entire system with the carrier gas, among other functions. If it is desired to employ the same system for calibrating as for analyzing gas samples, the calibration gases could be introduced through an appropriate valve near the outlet of probe 40 rather than at valve 70.

An adjustable throttle or metering valve 72 with a flow meter 74 permits setting the flow rate of the sample gas, or other gases, in accordance with the desired rate of flow through the chamber 24. Normally the gas sample flow rate through chamber 24 has no effect on the diffusion rate unless the flow rate becomes negative or drops below a certain minimum. This minimum flow rate may be determined for the particular membrane and sample gas combination by gradually increasing the sample gas flow rate until the point is reached where further increases have no effect on analyzer results. For example, given the particular cell and gas parameters previously described, the flow rate for maintaining the desired minimum pressure would be about 50 cubic centimeters per minute for the 38.8 cubic centimeters volume of chamber 24.

Without relatively high concentrations of the gas to be analyzed in the sample, such as are present in most stack gas applications, the pump 56 should be connected in the vent line 68, such as at position 80, and relief valve 58 omitted, in order to draw rather than push sample gas through the chamber 24, thus avoiding small concentration losses in the pump. For example, in monitoring ambient air pollutants, even very small amounts of $SO_2$ lost in the pump could constitute a significant proportion of the total anaylzer results. Where the pump 56 is placed after the cell 10 at position 80, a flow restriction valve should be connected in line 68 at position 82 to regulate the amount of pull from the pump which is seen by chamber 24 and a by-pass valve should be connected to conduit 42 at position 84 to reduce the retention of the system to a minimum.

Automatic controls might be employed at various points to respond to and correct for undesirable conditions. For example, an automatic back-flush cycle could be triggered to clean the probe 40 whenever the readings of vacuum gauge 60 dropped below a certain point. Or when flow meter 74 showed a certain minimum sample gas flow rate, the system might automatically shut down or sound an alarm.

THE HEATING SYSTEM

Referring to FIG. 6, conduit 42 has an interior tube 44, composed of Teflon, stainless steel or the like, encircled by insulated resistance heating wires 46. Tube 44 and heating elements 46 are surrounded by insulation 48 enclosed in an outer protective jacket 50 of polyvinyl chloride or the like. A thermistor 52 affixed to the outer wall of tube 44 is electrically connected to a suitable control unit 54 (FIG. 1) that varies the current supplied to the heating elements 46 to maintain the desired temperature above the dew point of the sample gas.

The cell 10, the unwrapped cell inlet tubes 44, valves 70 and 72, and flow meter 74 are all enclosed within the oven 86 to insure that the sample temperature remains above the dew point until it passes through the chamber 24. Preferably the oven has an open-bottomed rectangular steel housing 88 (FIG. 2) lined on its four sides and top with an insulating material 90, such as polyurethane. The housing 88 is secured to a base plate 92 by four threaded bolts 94 extending upward from an associated support leg 96 at each corner to pass through apertures in corner flanges 98 formed integrally with the housing 88. Wing nuts 100 are tightened on the threaded upper ends of bolts 94 to bear against flanges 98 clamping a rubber gasket 102 between the lower periphery of the housing 88 and the support plate 92 to limit heat losses from oven 86.

Heating pads 104 are mounted within the housing 88 on aluminum support legs 106 to the top and on each of the oven's four side walls. The heating pads 104 consist of high resistance electrical wires surrounded by silicon-rubber electrical insulating material. A fan 108 driven by moto 110 mounted on base plate 92 circulates the heat radiated from the pads 104 to maintain a homogenous temperature distribution throughout the oven interior. Insulation 90 is also provided around fan motor 110 on the lower side of support plate 92. A thermistor 112 positioned in the lower cell chamber 24 (FIG. 4) senses the temperature in the cell 10 and is connected so that the current to heating pads 104 is regulated by a proportional heat control unit 114 to maintain the desired temperature above the dew point of the sample gas. Thus, any temperature variations in the initial sample are corrected before reaching the cell 10 so that the membrane permeation rate will remain constant, provided that the time needed for the gas to pass through the heated conduit 42 and tube 44 before reaching the inlet port 20 is sufficient to allow it to reach the desired temperature. Usually the gas sample is heated above its stack temperature in the conduit 42 and is raised to an even higher temperature in the oven 86.

In order to prevent condensation from running back into chamber 24, vent line 68 is also heated to temperatures above the dew point under control of the heat control unit 54.

The diluted gas sample obtained from the diffusion cell 10 passes through a line 132 that allows it to cool to about room temperature before reaching the gas analyzers 146 since the high oven temperature could damage or disable most analyzers. Since little water remains in the diluted sample, and the dew point temperature is further lowered where a dry carrier gas is employed for dilution, condensation will not occur in line 132.

THE CARRIER GAS SYSTEM

A carrier gas flows through conduit 130 to upper chamber 30 where it passes across the top of membrane 38 to dilute the gas that diffuses through the membrane 30. The diluted sample emerges from the outlet port 28 to be conveyed through the line 132 to the analyzers 146. Besides providing a transport medium for the diffused gases, dilution by the carrier gas serves to prolong the operating life of certain analyzers in monitoring heavy pollutant concentrations where, with electrochemical analyzers, some active analyzer component is consumed at a rate corresponding to gas concentration being detected. Furthermore by using a dry carrier gas, the total water vapor concentration is further reduced to lower the dew point temperature in the upper chamber 30 and in line 132.

The carrier gas can be either ambient air drawn from the surrounding atmosphere or preferably an inert gas supplied under pressure. Where suitable, a pump 132 draws air from the atmosphere through conduit 130. A pressure regulator 136 maintains the downstream air at only a small percentage, such as 10%, of the pressure developed at the pump outlet, thus maintaining a constant flow rate through a scrubber 138 in spite of minor pressure variations from the pump 134. The scrubber 138 may contain desiccants, activated carbon filters or the like for removing water vapor, pollutants and other gases which might change or interfere with concentrations in the diffused gas or perhaps even react with the diffused gas. This provides a constant supply of clean air as the carrier gas for the upper diffusion cell chamber 30 to proportionately dilute the concentrations of diffused gas reaching the analyzers.

Pressure regulators 139 and 140 allow carrier gas to flow through lines 130 and 120 respectively at predetermined rates in order to maintain the same flow through chamber 30 even when part of the carrier gas is diverted through line 120. A metering or throttle valve 141 may be used in conjunction with a flow meter 142 to regulate the precise carrier gas flow rate into the chamber 30. Alternatively, the flow meter 142 might be replaced by an automatic constant flow metering device that could automatically maintain a precise constant flow rate or by a mass flow meter that could record pressure variations as well.

When the carrier gas is an inert gas obtained from a pressurized source, such as a cylinder or tank, it may be delivered directly through a pressure regulator 136 at a constant flow rate to the chamber 30.

With the exemplary system parameters given hereinbefore, a dry carrier gas flow rate of about 1.0 cu. ft. per hr. is suitable for providing a retention time in chamber 30 of about 0.67 seconds, where the chamber has a volume of about 5.3 cubic centimeters, and for delivering an $SO_2$ concentration of about 20 ppm to the analyzers 146 with less than about 0.2% water vapor concentration, where the original gas sample had a water vapor concentration of about 10%, that for all practical purposes is considered a dry gas sample. this eliminates the necessity for various water content tests and analyzer result corrections required by governmental agencies, such as Air Pollution Control Districts and the Environmental Protection Agency, where substantial amounts of water remain in the gas sample supplied to the analyzer.

The system of FIG. 1 may also be used, instead of the conventional permeation tube, as a variable source for supplying specified concentrations of particular gases at selected temperatures to be used in calibrating analyzers and the like. As temperature increases, so does the rate of diffusion or release of gas through the permeable membrane material used in the conventional permeation tubes. Such tubes however emit only limited gas concentrations and are capable of holding only limited volumes. In contrast, with this system the concentration of the particular gas obtained from outlet port 28 may be readily varied over almost any range simply by adjusting the carrier gas flow rate, chamber size, number of chambers or membranes, membrane area or type, or other factors. Also, the operating temperature may be adjusted to obtain the desired membrane temperatures, and the system has a practically unlimited operational life where the available supply of the particular calibration gas is not limited.

In this regard, the sections 12 and 14 can be secured with easily removable clamps, rather than the bolts 16, to facilitate changing the membrane 32 to vary the concentration of gases supplied to various analyzers for calibration. In addition, the probe 40, pumps 56 and 62, valves 58 and 66, and gauge 60 can be omitted for this purpose, and valve 70 may be replaced with a four position valve. Also the entire heating system is unnecessary except for that portion used to maintain the membrane 32 at a relatively constant temperature level consistent with the desired permeation rates.

Thus, a system is provided which reduces membrane fouling, supplies analyzers with a clean, dry representative gas sample and is easily disassembled for membrane replacement if necessary.

It will be understood that the disclosed embodiment of this invention may be modified in various ways and employed with a variety of analyzers to monitor different gases and for many other purposes within the scope of the appended claims.

What is claimed is:
1. A system for preparing a gas sample for measurement of high concentrations of one or more selected gaseous components in a gas stream from a pollutant source, such as an industrial stack, containing particulate matter, water vapor and the like at higher than ambient temperatures, comprising:
   a cell structure defining first and second gas retention chambers, each of said chambers having separate gas inlet and outlet ports;
   a semipermeable membrane impervious to water vapor and particulate matter for separating said chambers and allowing diffusion of the selected gaseous components therethrough at a rate corresponding to the partial pressure of said component in said sample;
   a porous probe means adapted to be disposed in said gas stream collecting a representative gas sample while excluding most particulate matter from the sample;
   temperature controlled conduit means for maintaining the sample from said probe at temperatures above its maximum dew point and for introducing said sample to pass through said first chamber at a substantially constant predetermined temperature above said maximum dew point;
   temperature control means, including an oven surrounding said cell structure, for maintaining said membrane and the cell structure defining said chambers at a substantially constant homogeneous temperature above said maximum dew point;
   means for supplying a flow of carrier gas to said second chamber at a substantially constant rate to dilute the selected gaseous components diffusing through the membrane from the first into the second chamber; and,
   means for conveying the mixture of said carrier gas and said diffused gaseous components from the second chamber to provide a clean, substantially dry gas mixture having a concentration of said selected components corresponding to the concentration in the gas sample from said source.
2. A system for preparing a gas sample for measurement of high concentrations of one or more selected gaseous components in a gas stream from a pollutant source, such as an industrial stack, containing particulate matter, water vapor and the like at higher than ambient temperatures, comprising:
   a sealed cell having upper and lower portions defining upper and lower contiguous chambers, each of said chambers having separate gas inlet and outlet ports;
   a semipermeable membrane separating said chambers to permit diffusion of selected gaseous components while being impervious to water vapor and particulate matter;
   porous probe means for collecting a gas sample from the pollutant source and excluding most particulate matter from the sample;
   temperature controlled conduit means for conveying said gas sample from said probe at temperatures above its maximum dew point to be delivered to said lower chamber at a substantially constant temperature above said maximum dew point approximating the temperature of said membrane;

means for supplying a substantially constant flow of a carrier gas to the upper chamber to dilute the selected gases that diffuse into the upper chamber;

means for conveying the carrier gas with said diluted selected gases from the upper chamber; and, temperature control means, including an oven surrounding said cell, for maintaining said membrane and said chambers at a substantially constant homogeneous temperature above said maximum dew point, whereby a clean, substantially water-free diffused gas sample emerges from said upper chamber without any gas sample loss due to water condensation.

3. A system for preparing a gas sample as defined in claim 2, wherein said temperature control means includes a circuit responsive to a thermistor positioned in said lower chamber to sense temperature variations within said lower chamber; and, said conveying means includes a pump connected to said lower chamber outlet port to draw sample gas from said probe through the lower chamber.

4. A system for preparing a gas sample as defined in claim 3, wherein:

said pump is operated to maintain a minimum flow rate of sample gas through said lower chamber in excess of predetermined level at which diffusion of the selected gas components could vary, whereby said selected gas components diffuse through said membrane into said second chamber at a rate proportional to their concentration in said sample.

5. A system for preparing a gas sample for measurement of concentrations of one or more selected gaseous components in a gas stream from a pollutant source, such as an industrial stack, containing particulate matter, water vapor and the like at higher than ambient temperatures, comprising:

a sealed cell having upper and lower portions defining upper and lower contiguous chambers, each of said chambers having separate gas inlet and outlet ports;

a semipermeable membrane separating said chambers, said membrane being substantially horizontally disposed between said chambers permitting diffusion of the selected gaseous components therethrough but being impermeable to water vapor and particulate matter;

a porous probe means for collecting a representative gas sample from the pollutant source while excluding substantially all particulate matter from the sample;

temperature controlled conduit means for conducting the sample from said probe at temperatures above its maximum dew point to be delivered to said lower chamber at a substantially constant temperature above said maximum dew point and at a predetermined minimum flow rate in excess of the rate at which a decreased flow would substantially alter the rate of diffusion of said selected gases through the membrane from the lower to the upper chamber;

means for supplying a substantially constant flow of carrier gas, free of interfering gases and water vapor, to the upper chamber to dilute the selected gases that diffuse into said upper chamber;

means for conveying the carrier gas and said diluted selected gases from the upper chamber to a gas analyzer; and, oven means surrounding said cell and at least a portion of said gas sample conveying means for maintaining said cell and the gas sample within said lower chamber at a substantially constant homogeneous temperature above the maximum dew point of said sample, whereby a clean, substantially water-free diffused gas sample is supplied for analysis without loss due to water condensation.

6. A system for preparing a gas sample as defined in claim 5, further comprising:

a temperature control curcuit connected to said oven, including a thermistor positioned in said cell lower chamber, for adjusting the temperature within said oven in inverse proportion to temperature variations within said lower chamber, and a pump connected to said lower chamber outlet port to draw sample gas from said probe through the lower chamber above a predetermined minimum rate.

7. A system for preparing a gas sample as defined in claim 6, wherein:

said probe has porous sintered steel walls through which representative gas samples are collected substantially free of particulate matter.

8. A system for preparing a gas sample as defined in claim 7, further comprising:

support pads clamped against the upper and lower surfaces of the membrane, said support pads having a porosity sufficient to allow the free flow of selected gases therethrough and consisting of a material that is non-reactive with the selected gases.

9. A system for preparing a gas sample as defined in claim 8, further comprising:

means for selectively directing a pressurized gas flow through a portion of said temperature controlled conduit means in the reverse direction relative to the normal flow of sample gas to purge said probe of particulate matter.

10. A system for preparing a gas sample as defined in claim 9, wherein:

said means for conveying the carrier gas and diluted selected gases from the upper chamber includes means for cooling the gases to a temperature suitable for gas analysis.

* * * * *